United States Patent
Tracy et al.

(10) Patent No.: US 11,629,365 B2
(45) Date of Patent: *Apr. 18, 2023

(54) STARCH AQUEOUS FERMENTATION FEEDSTOCK AND A METHOD FOR THE PRODUCTION THEREO

(71) Applicant: SUPERBREWED FOOD INC., New Castle, DE (US)

(72) Inventors: Bryan P. Tracy, Wilmington, DE (US); Dale A. Monceaux, Loveland, OH (US); Aharon M. Eyal, Jerusalem (IL); Sasson R. Somekh, Los Altos Hills, CA (US)

(73) Assignee: SUPERBREWED FOOD INC., New Castle, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/272,319

(22) PCT Filed: Aug. 27, 2019

(86) PCT No.: PCT/IB2019/057220
§ 371 (c)(1),
(2) Date: Feb. 28, 2021

(87) PCT Pub. No.: WO2020/044242
PCT Pub. Date: Mar. 5, 2020

(65) Prior Publication Data
US 2021/0180100 A1    Jun. 17, 2021

Related U.S. Application Data

(60) Provisional application No. 62/723,004, filed on Aug. 27, 2018.

(51) Int. Cl.
| | | |
|---|---|---|
| *C12N 1/14* | (2006.01) | |
| *C12N 1/16* | (2006.01) | |
| *C12N 1/20* | (2006.01) | |
| *C12N 1/22* | (2006.01) | |
| *C12P 19/14* | (2006.01) | |
| *C12P 7/10* | (2006.01) | |
| *C12P 19/02* | (2006.01) | |
| *C12P 19/20* | (2006.01) | |

(52) U.S. Cl.
CPC .............. *C12P 19/14* (2013.01); *C12N 1/14* (2013.01); *C12N 1/16* (2013.01); *C12N 1/20* (2013.01); *C12P 7/10* (2013.01); *C12P 19/02* (2013.01); *C12P 19/20* (2013.01)

(58) Field of Classification Search
None
See application file for complete search history.

(56) References Cited

U.S. PATENT DOCUMENTS

| | | | |
|---|---|---|---|
| 11,447,799 B2* | 9/2022 | Tracy | C12P 19/04 |
| 2015/0211026 A1* | 7/2015 | Bazzana | C12P 7/10 |
| | | | 435/141 |
| 2019/0284649 A1* | 9/2019 | Jakel | C12P 7/649 |
| 2021/0180100 A1* | 6/2021 | Tracy | C12P 7/10 |

OTHER PUBLICATIONS

Scepter Stainless Steel Membrane, Proven Technology for the Most Challenging Separations. https://www.gravertech.com/product-lines/crossflow-membrane/scepter-tubular-mf-and-uf-modules/scepter-membrane-module-assemblies/scepter-membrane-module-assemblies-brochure/, GTX-182-rev, pp. 1-8 (2007). (Year: 2007).*

* cited by examiner

*Primary Examiner* — Richard C Ekstrom
(74) *Attorney, Agent, or Firm* — Eva Taksel

(57) ABSTRACT

Provided are aqueous fermentation feedstocks comprising glucose monomers at a concentration of less than 50 gram/Liter (g/L) of the total feedstock, water-soluble dextrose oligomers at a concentration in a range between 50 g/L and 300 g/L of the total feedstock; and water. Further provided are methods of production thereof and uses thereof in the production of single cell protein and/or ethanol.

12 Claims, No Drawings

STARCH AQUEOUS FERMENTATION FEEDSTOCK AND A METHOD FOR THE PRODUCTION THEREO

FIELD OF THE INVENTION

The field of art to which this invention generally pertains is feedstock, and more specifically to aqueous fermentation feedstock, methods of production thereof and uses thereof.

BACKGROUND OF THE INVENTION

The cost of fermentation feedstock is a major contributor to the cost of fermentation products. There is, therefore, a strong need for a low cost fermentation feedstock and for methods of production thereof.

SUMMARY OF THE INVENTION

According to an aspect of some embodiments of the present invention provided is an aqueous fermentation feedstock comprising:
(i) glucose monomers at a concentration of less than 50 gram/Liter (g/L) of the total feedstock:
(ii) water-soluble dextrose oligomers at a concentration in a range between 50 g/L and 300 g/L of the total feedstock; and
(iii) water.

According to an embodiment, the aqueous fermentation feedstock further comprises at least one selected from the group consisting of
(i) slurried particles of a starchy gran having a greatest dimension of less than 0.5 micron;
(ii) slurried particles of a starchy grain having a greatest dimension of more than 0.5 micron, wherein the content of such suspended particles is less than 30 g/L of the total feedstock;
(iii) inorganic mineral content at a concentration in a range between 2 g/L and 50 g/L of the total feedstock;
(iv) lactate at a concentration in a range between 0.5 g/L and 10 g/L of the total feedstock;
(v) protein at a concentration in a range between 5 g/L and 50 g/L of the total feedstock;
(vi) vegetable oil at a concentration of less than 10 g/L of the total feedstock; and
(vii) glycerol at a concentration in a range between 1 g/L and 30 g/L of the total feedstock,
or combinations thereof.

According to an embodiment, the aqueous fermentation feedstock is sterile.

According to an aspect of some embodiments of the present invention, provided is a method for producing the aqueous fermentation feedstock disclosed herein, the method comprising
(i) providing a starchy grain;
(ii) comminuting said starchy grain to form comminuted starchy grain;
(iii) adding water to said comminuted starchy grain to form an aqueous slurry of said comminuted starchy grain;
(iv) hydrolytically treating said aqueous slurry at a temperature greater than 25 degrees Celsius to form a starchy mash comprising said water soluble dextrose oligomers, said glucose monomers and water-insoluble carbohydrates; and
(v) filtering at least a fraction of said starchy mash through a microfiltration membrane to form an aqueous filtration permeate consisting of said aqueous fermentation feedstock and a filtration retentate comprising said water-insoluble carbohydrates.

According to an embodiment, the duration of said hydrolytically treating said aqueous slurry is in a range between 30 minutes and 300 minutes.

According to an embodiment, said method further comprises grinding of said aqueous slurry.

According to an embodiment, said method further comprises jet-cooking of said aqueous slurry.

According to an embodiment, said hydrolytically treating comprises treating said aqueous slurry with at least one alpha-amylase enzyme.

According to an embodiment, said microfiltration membrane is selected from the group consisting of sintered stainless steel membranes, polymeric membranes and ceramic membranes.

According to an embodiment, said microfiltration membrane is sintered stainless steel membrane with ceramic coating. According to some such embodiments, said ceramic coating comprises titanium oxide.

According to an embodiment, said microfiltration membrane has a pore size in a range between 0.01 micron and 0.5 micron.

According to an embodiment, said method further comprising washing said retentate with an aqueous washing solution to form a washed retentate and a wash solution, separating said washed retentate from said wash solution, and adding said wash solution to the aqueous fermentation feedstock.

According to an embodiment, said aqueous washing solution comprises water soluble dextrose oligomers.

According to an embodiment, said forming an aqueous slurry comprises blending at least a fraction of said separated wash solution with said comminuted starchy grain.

According to an embodiment, said filtering is carried out according to at least one condition selected from the group consisting of
(i) processing temperature ranging between 37 and 100 degrees Celsius;
(ii) feed pressure ranging between 2 and 10 atmospheres;
(iii) retentate pressure ranging between 2 and 10 atmospheres;
(iv) permeate pressure ranging between 1 and 8 atmospheres;
(v) circulation or feed flow rate that creates a linear velocity within the membranes of at least 5 feet per second; and
(vi) transmembrane pressure drop ranging between 1 and 10 atmospheres, or combinations thereof.

According to an aspect of some embodiments of the present invention, provided is a method for the production of single-cell protein, comprising culturing selected organisms in an aqueous fermentation feedstock as disclosed herein.

According to an embodiment, said selected organisms comprise at least one organism selected from the group consisting of *Butyribacterium methylotrophicum* and *Clostridium tryobutyricum.*

According to an embodiment, a single-cell protein production yield is in a range between 120 gram and 350 gram per Kilogram of water-soluble dextrose oligomers in said aqueous fermentation feedstock.

According to an aspect of some embodiments of the present invention, provided is method for the production of single-cell protein and ethanol, comprising producing an aqueous fermentation feedstock according to the method disclosed herein, further comprising fermenting said aqueous fermentation feedstock with at least one organism selected from the group consisting of *Butyribacterium methylotrophicum* and *Clostridium tryobutyricum* to form single cell protein and fermenting said filtration retentate with *Saccharomyces cerevisiae* to form ethanol.

DETAILED DESCRIPTION OF THE INVENTION

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description making apparent to those skilled in the art how the several forms of the invention may be embodied in practice.

The present invention will now be described by reference to more detailed embodiments. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

Unless indicated otherwise, percent is weight percent and ratio is weight/weight ratio. Unless indicated otherwise, weight ratio means the ratio between weight content.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

Additional advantages of the invention will be set forth in part in the description, which follows, and in part will be obvious from the description, or may be learned by practice of the invention. It is to be understood that both the foregoing general description and the following detailed description are exemplary and explanatory only and are not restrictive of the invention, as claimed.

As used herein, the term "fermentation feedstock" refers to a biological material for use in a fermentation process as an energy source for a microorganism for preparation of a product for use as an animal feed.

As used herein, the term "aqueous fermentation feedstock" refers to a biological material for use in a fermentation process as an energy source for a microorganism for preparation of a product for use as an animal feed, wherein the product comprises at least 50% (w/w) water.

As used herein, the term "SCP" refers to Single-Cell Protein

As used herein, the term "oligomers" refers to molecules comprising 2-30 monomer units. As used herein, the term "dextrose oligomers" refers to molecules wherein the monomer units are D-glucose monomers.

As used herein, the term "slurried particles" refers to particles suspended in a liquid.

As used herein, the term "comminuting" refers to reducing to particles of greatest dimension no greater than about 1 mm. According to some embodiments, comminuting comprises one or more selected from the group consisting of crushing, milling and grinding.

As used herein, the term "hydrolytically treating" refers to treating directed to hydrolyzing starch molecules in a slurry According to an aspect of some embodiments of the present invention provided is an aqueous fermentation feedstock comprising:
 (i) glucose monomers at a concentration of less than 50 gram/Liter (g/L) of the total feedstock:
 (ii) water-soluble dextrose oligomers at a concentration in a range between 50 g/L and 300 g/L of the total feedstock; and
 (iii) water.

According to an embodiment, the aqueous fermentation feedstock further comprises at least one selected from the group consisting of
 (i) slurried particles of a starchy grain having a greatest dimension of less than 0.5 micron;
 (ii) slurried particles of a starchy grain having a greatest dimension of more than 0.5 micron, wherein the content of such suspended particles is less than 30 g/L of the total feedstock;
 (iii) inorganic mineral content at a concentration in a range between 2 g/L and 50 g/L of the total feedstock;
 (iv) lactate at a concentration in a range between 0.5 g/L and 10 g/L of the total feedstock;
 (v) protein at a concentration in a range between 5 g/L and 50 g/L of the total feedstock;
 (vi) vegetable oil at a concentration of less than 10 g/L of the total feedstock; and
 (vii) glycerol at a concentration in a range between 1 g/L and 30 g/L of the total feedstock,
 (viii) or combinations thereof.

According to an embodiment, said dextrose oligomers comprise dextrose oligomers of any degree of polymerization (DP), e.g. DP2, DP3, DP4 and higher degrees of polymerization, e.g. DP10 or DP20. According to an embodiment, said dextrose oligomers comprise dextrins.

According to an embodiment, said aqueous fermentation feedstock comprises glucose monomers at a concentration of less than 50 g/L of the total feedstock, less than 40 g/L, less than 30 g/L, less than 20 g/L, less than 10 g/L or less than 5 g/L of the total feedstock. According to an embodiment, the concentration of the dextrose oligomers in said fermentation feedstock is in a range between 50 g/L and 300 g/L of the total feedstock, between 60 g/L and 200 g/L, between 70 g/L and 180 g/L or between 80 g/L and 150 g/L of the total feedstock. According to an embodiment, the concentration of the dextrose oligomers in said aqueous fermentation feedstock is greater than 50 g/L of the total feedstock, greater than 60 g/L, greater than 70 g/L, greater than 80 g/L, greater than go g/L, greater than 100 g/L, greater than 110 g/L, or greater than 120 g/L of the total feedstock.

According to an embodiment, said aqueous fermentation feedstock is clear i.e. substantially transparent, having a high level of light transmittance.

According to an embodiment, said fermentation feedstock comprises slurried particles of a starchy grain, such as corn and/or milo. According to an embodiment, said particles are of less than 0.5 micron, such as 0.01 micron, 0.05 micron, 0.1 micron, 0.2 micron, 0.3 micron, or 0.4 micron. According to an embodiment, said particles are of more than 0.01 micron, 0.05 micron, 0.1 micron, 0.5 micron, such as 1 micron, 2 micron, or 5 micron, and the content of such slurried particles of more than 0.5 micron is less than 30 g/L, less than 20 g/L or less than 10 g/L of the total feedstock.

According to an embodiment, said fermentation feedstock comprises one or more selected from the group consisting of inorganic minerals, lactate, protein, vegetable oil and glycerol, or combinations thereof. According to an embodiment the concentration of inorganic minerals is in a range between 2 g/L and 50 g/L, between 5 g/L and 45 g/L or between 10 g/L and 40 g/L of the total feedstock. According to an embodiment, lactate concentration is in a range between 0.5 g/L and 10 g/L, between 1 g/L and 8 g/L or between 2 g/L and 6 g/L of the total feedstock. According to an embodiment, protein concentration is in a range between 5 g/L and 50 g/L, between 10 g/L and 40 g/L or between 20 g/L and 30 g/L of the total feedstock. According to an embodiment, vegetable oil concentration is less than 10 g/L, less than 8 g/L or less than 6 g/L of the total feedstock. According to an embodiment, said vegetable oil comprises at least one of corn oil and milo (sorghum) oil. According to an embodiment, glycerol concentration is in a range between 1 g/L and 30 g/L, between 2 g/L and 25 g/L or between 3 g/L and 20 g/L of the total feedstock.

According to an embodiment, said aqueous fermentation feedstock is sterile. The aqueous fermentation feedstock may be sterilized by any method known in the art, such as, for example, by microfiltration and/or steam sterilization (i.e., autoclaving).

According to an embodiment, said aqueous fermentation feedstock has a specific gravity greater than 1.05, such as 1.1, 1.15, or 1.2.

According to an embodiment, said aqueous fermentation feedstock is has a yellow to brown color.

According to an aspect of some embodiments of the present invention, provided is a method for producing the aqueous fermentation feedstock disclosed herein, the method comprising
(i) providing a starchy grain;
(ii) comminuting said starchy grain to form comminuted starchy grain;
(iii) adding water to said comminuted starchy grain to form an aqueous slurry of said comminuted starchy grain;
(iv) hydrolytically treating said aqueous slurry at a temperature greater than 25 degrees Celsius to form a starchy mash comprising said water soluble dextrose oligomers, said glucose monomers and water-insoluble carbohydrates; and
(v) filtering at least a fraction of said starchy mash through a microfiltration membrane to form an aqueous filtration permeate consisting of said aqueous fermentation feedstock and a filtration retentate comprising said water-insoluble carbohydrates.

According to an embodiment, said starchy grain comprises at least one of corn and milo (sorghum).

According to an embodiment, said hydrolytically treating breaks down starch (e.g. amylose and/or amylopectin) into fractions with a degree of polymerization of less than 200 or less than 100, such as less than 50, less than 10, or less than 5.

According to an embodiment, said hydroloytically treating comprises contacting said slurry with at least one alpha-amylase enzyme.

According to an embodiment, the duration of said hydrolytically treating is in a range between 30 minutes and 300 minutes, between 60 minutes and 240 minutes or between go minutes and 160 minutes. According to an embodiment, the duration of said hydrolytically treating is greater than 30 minutes; greater than 40 minutes, greater than 50 minutes; greater than 60 minutes, greater than 70 minutes; greater than 80 minutes; greater than 90 minutes or greater than 100 minutes.

According to an embodiment, said hydrolytically treating is conducted at a temperature greater than 30 degrees Celsius, greater than 35 degrees Celsius, greater than 40 degrees Celsius, greater than 45 degrees Celsius, or greater than or about 50 degrees Celsius.

According to an embodiment, said method further comprises at least one of grinding said aqueous slurry and jet-cooking of said aqueous slurry. According to an embodiment, said grinding and/or jet-cooking is conducted using apparatus and conditions similar to those used in corn dry milling.

According to an embodiment, said grinding of said aqueous slurry is carried out using a hammer mill to produce particles having a greatest dimension of no greater than 1 mm.

According to an embodiment, said method comprises separating at least a fraction of said starchy mash into an aqueous portion and a water-insoluble portion, wherein the aqueous portion comprises said water-soluble dextrose oligomers and glucose monomers, and the water-insoluble portion comprises water-insoluble carbohydrates.

According to an embodiment, said separating comprises at least one of centrifugation, micro-filtration and ultra-filtration, or combinations thereof.

According to an embodiment, said method comprises filtering at least a fraction of said starchy mash through a microfiltration membrane. According to an embodiment, said filtering comprises feeding said starchy mash to a microfiltration unit comprising at least one microfiltration membrane. Said fed starchy mash, comprising water-soluble carbohydrates and water-insoluble carbohydrates, is also referred to as filtration feed. According to an embodiment, said filtering generates an aqueous filtration permeate, comprising said water-soluble carbohydrates and said glucose monomers, and a filtration retentate comprising said water-insoluble carbohydrates. According to an embodiment, said method further comprises separating said filtration permeate from said filtration retentate, to form separated permeate and separated retentate. Any form of separating is suitable.

According to an embodiment, a feed flow rate is in a range between 0.3 and 1.2 gallon per minute per square feet of the membrane, between 0.4 and 1.1, or between 0.5 and 1 gallon per minute per square feet. According to an embodiment, permeate flow rates to is in a range between 0.01 and 0.1 gallon per minute per square feet of the membrane.

According to an embodiment, said filtering is carried out at a processing temperature (i.e. feed, permeate and retentate temperature) ranging between 37 and 100 degrees Celsius, between 50 and 80 or between 55 and 70 degrees Celsius. According to an embodiment, said filtering is carried out at a feed pressure ranging between 2 and 10 atmospheres gauge, between 3 and 8 or between 4 and 6 atmospheres. According to an embodiment, said filtering is carried out at a retentate pressure ranging between 2 and 10 atmospheres, between 3 and 8 or between 4 and 6 atmospheres. According to an embodiment, said filtering is carried out at a permeate pressure ranging between 1 and 8 atmospheres, between 2 and 7 or between 3 and 6 atmospheres. According to an embodiment, said filtering is carried out with a transmembrane pressure drop ranging between 1 and 10 atmospheres, between 2 and 9 or between 3 and 8 atmospheres. According to an embodiment, said filtering comprises circulation or feed flow rate that creates a linear velocity within the membranes of at least 5 feet per second.

According to an embodiment, said microfiltration membrane is selected from the group consisting of sintered stainless steel membranes, polymeric membranes and ceramic membranes. According to an embodiment, said polymeric membranes are in hollow-fiber, in spiral wound and/or in plate and frame form. According to an embodiment, said microfiltration membrane is a sintered stainless steel membrane with ceramic coating. According to an embodiment, said ceramic coating comprises titanium oxide. According to an embodiment, said microfiltration membrane has a pore size in a range between 0.01 micron and 0.5 micron, between 0.01 micron and 0.4 micron, between 0.01 micron and 0.3 micron, between 0.02 micron and 0.2 micron or about 0.1 micron.

According to an embodiment, said method further comprising washing said retentate with an aqueous washing solution to form a washed retentate and a wash solution, separating said washed retentate from said wash solution, and adding said wash solution to the aqueous fermentation feedstock.

According to an embodiment, said forming an aqueous slurry comprises blending at least a fraction of said separated wash solution with comminuted starchy grain.

According to an aspect of some embodiments of the present invention, provided is a method for the production of single-cell protein, comprising culturing selected organisms in an aqueous fermentation feedstock as disclosed herein.

According to an embodiment, said selected organisms comprises at least one organism selected from the group consisting of *Butyribacterium methylotrophicum* and *Clostridium tryobutyricum*.

According to an embodiment, a single-cell protein production yield is in a range between 120 gram and 350 gram per Kilogram of water-soluble dextrose oligomers in said aqueous fermentation feedstock.

According to an embodiment, said culturing comprises metabolizing at least a fraction of said water-soluble dextrose oligomers and optionally also at least a fraction of said glycerol and/or said lactate, if present.

According to an embodiment, said culturing is conducted in at least one mode selected from the group consisting of batch, batch simultaneous saccharification and fermentation (SSF), fed batch, fed batch SSF, continuous and continuous SSF.

According to an embodiment, said method further comprises separating at least a fraction of said single-cell protein. According to an embodiment, provided is a protein feed ingredient comprising said single-cell protein. According to an embodiment, provided is a protein feed ingredient comprising said single-cell protein and at least a fraction of the protein in said fermentation feedstock.

According to an aspect of some embodiments of the present invention, provided is method for the production of single-cell protein and ethanol, comprising producing an aqueous fermentation feedstock according to the method disclosed herein, further comprising fermenting said aqueous fermentation feedstock with at least one organism selected from the group consisting of *Butyribacterium methylotrophicum* and *Clostridium tryobutyricum* to form single cell protein and fermenting said filtration retentate with *Saccharomyces cerevisiae* or another ethanol-producing microorganism to form ethanol.

According to an embodiment, the method comprises providing said retentate to a mash cooler/beer preheater heat exchanger and then to ethanol fermentation. According to an embodiment, the method comprises providing said retentate to a mash cooler heat exchanger and then to a bio-catalytic or thermo-mechanical conversion or to a drying or to a subsequent mechanical fractionation process.

EXAMPLE

This example illustrates the generation of an aqueous fermentation feed and subsequent fermentation to generate a single-cell protein. To prepare the aqueous fermentation feed, a corn mash was first prepared. The corn mash was made by grinding corn in a hammermill to about 1 mm in diameter, mixing the ground corn with water into a slurry until a total solids percentage of 36% (g/g) is achieved, adding an alpha-amylase to the slurry, and then cooking the slurry at 87-88° C. The corn mash was then diluted by half to a total solids percentage of about 18% (g/g) and fed into a microfiltration skid. The microfiltration skid was made up of Spector® membranes, $TiO_2$-coated sintered stainless steel membranes, manufactured by Graver Technologies with a pore size of 0.1 micron. The system was run at 2.4 atm and 65° C. The permeate, consisting of soluble dextrose oligomers, glucose monomers, and water, was sent to the fermentation vessel, while the retentate was washed twice with water. The washes were also sent to the fermentation vessel to achieve about 87% extraction of the soluble oligomers and monomers.

Trace vitamins and minerals were added to the fermentation at 10 mL per L of volume each. The vitamin solution consisted of 2 mg/L biotin, 2 mg/L folic acid, 10 mg/L pyridoxine-HCl, 5 mg/L thiamine-HCl, 5 mg/L riboflavin, 5 mg/L nicotinic acid, 5 mg/L calcium D-(+)-pantothenate, 0.1 mg/L vitamin B12, 5 mg/L p-aminobenzoic acid, and 5 mg/L thioctic acid, and the mineral solution consisted of 2 g/L nitrilotriacetic acid, 1 g/L $MnSO_4$—$H_2O$, 0.8 g/L $Fe(SO_4)_2(NH_4)_2.6H_2O$, 0.2 g/L $CoCl_2.6H_2O$, 0.2 mg/L $ZnSO_4.6H_2O$, 0.02 g/L $CuCl_2.2H_2O$, 0.02 g/L $NiCl_2.6H_2O$, 0.02 g/L $Na_2MoO_4.2H_2O$, 0.02 g/L $Na_2SeO_4$, and 0.02 g/L $Na_2WO_4$. The fermenter was inoculated with a single cell protein strain, *Clostridium tyrobutyricum*, and the reactor was operated at 35° C. and pH 6.0, with a 6M ammonium hydroxide base solution. After about 16 hours, the fermentation as exhausted, and the cell mass was collected and dried into a single cell protein product.

The invention claimed is:

1. A method for producing an aqueous fermentation feedstock comprising glucose monomers at a concentration of less than 50 gram/Liter (g/L) of the total feedstock; water-soluble dextrose oligomers at a concentration in a range between 50 gram/Liter and 300 gram/Liter of the total feedstock; and water, for growth of single cell proteins, the method comprising (i) providing a starchy grain;

(ii) comminuting said starchy grain to form comminuted starchy grain;

(iii) adding water to said comminuted starchy grain to form an aqueous slurry of said comminuted starchy grain;

(iv)hydrolytically treating said aqueous slurry at a temperature greater than 25 degrees Celsius to form a starchy mash comprising said water soluble dextrose oligomers, said glucose monomers and water-insoluble carbohydrates; and (v) filtering at least a fraction of said starchy mash through a hydrophobic microfiltration membrane selected from the group consisting of a sintered stainless steel membrane and a polymeric membrane to form an aqueous filtration permeate consisting of said aqueous fermentation feedstock, and a filtration retentate comprising said water-insoluble carbohydrates.

2. The method of claim 1, wherein the duration of said hydrolytically treating said aqueous slurry is in a range between 30 minutes and 300 minutes.

3. The method of claim 1, further comprising grinding of said aqueous slurry.

4. The method of claim 1, further comprising jet-cooking of said aqueous slurry.

5. The method of claim 1, wherein said hydrolytically treating comprises contacting said aqueous slurry with at least one alpha-amylase enzyme.

6. The method of claim 1, wherein said microfiltration membrane is sintered stainless steel membrane with ceramic coating.

7. The method of claim 6, wherein said ceramic coating comprises titanium oxide.

8. The method of claim 1, wherein said microfiltration membrane has a pore size in a range between 0.01 micron and 0.5 micron.

9. The method of claim 1, further comprising washing said retentate with an aqueous washing solution, to form a washed retentate and a wash solution, separating said washed retentate from said wash solution and adding said wash solution to the aqueous fermentation feedstock.

10. The method of claim 9, wherein said aqueous washing solution comprises water soluble dextrose oligomers.

11. The method of claim 9, wherein said forming an aqueous slurry comprises blending at least a fraction of said separated wash solution with said comminuted starchy grain.

12. The method of claim 2, wherein said filtering is carried out according to at least one condition selected from the group consisting of (i) processing temperature ranging between 37 and 100 degrees Celsius;

(ii) feed pressure ranging between 2 and 10 atmospheres;

(iii) retentate pressure ranging between 2 and 10 atmospheres;

(iv) permeate pressure ranging between 1 and 8 atmospheres;

(v) circulation or feed flow rate that creates a linear velocity within the membranes of at least 5 feet per second; and (vi)transmembrane pressure drop ranging between 1 and 10 atmospheres or combinations thereof.

* * * * *